(12) United States Patent
Dennis et al.

(10) Patent No.: US 8,669,346 B2
(45) Date of Patent: Mar. 11, 2014

(54) BONE MARROW TARGETING PEPTIDES

(75) Inventors: James E. Dennis, Cleveland Heights, OH (US); Thomas Kean, Seattle, WA (US)

(73) Assignee: Case Western Reserve University, Cleveland, OH (US)

( * ) Notice: Subject to any disclaimer, the term of this patent is extended or adjusted under 35 U.S.C. 154(b) by 150 days.

(21) Appl. No.: 13/195,665

(22) Filed: Aug. 1, 2011

(65) Prior Publication Data

US 2012/0028350 A1 Feb. 2, 2012

Related U.S. Application Data

(60) Provisional application No. 61/369,236, filed on Jul. 30, 2010.

(51) Int. Cl.
| | |
|---|---|
| *C07K 7/06* | (2006.01) |
| *C07K 7/00* | (2006.01) |
| *C12N 5/16* | (2006.01) |
| *A61K 38/08* | (2006.01) |
| *A61K 35/28* | (2006.01) |
| *C12N 5/07* | (2010.01) |
| *C12N 5/0789* | (2010.01) |
| *C12N 5/074* | (2010.01) |

(52) U.S. Cl.
CPC ... *C07K 7/06* (2013.01); *C07K 7/00* (2013.01); *C12N 5/06* (2013.01); *C12N 5/0647* (2013.01); *C12N 5/0672* (2013.01)
USPC ........ 530/329; 530/300; 530/388.7; 435/325; 514/21.7

(58) Field of Classification Search
CPC ......... C07K 7/06; A61K 35/28; A61K 38/08; C12N 5/06; C12N 5/0647; C12N 5/0672; C12N 5/0678; C12N 5/68; C12N 5/0665; C12N 5/16
See application file for complete search history.

(56) References Cited

U.S. PATENT DOCUMENTS

2011/0182862 A1 * 7/2011 Green et al. ................. 424/93.5

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
SEQ ID No. 21339 from US 2011/0182862, Jul. 2011.*

* cited by examiner

*Primary Examiner* — Julie Ha
(74) *Attorney, Agent, or Firm* — Tarolli, Sundheim, Covell & Tummino LLP

(57) ABSTRACT

A peptide for targeting bone marrow consists of about 5 to about 25 amino acids and includes an amino acid sequence that targets the peptide to bone marrow.

7 Claims, 4 Drawing Sheets

SEQUENCE LISTING

```
<160> NUMBER OF SEQ ID NOS: 42

<210> SEQ ID NO 1
<211> LENGTH: 6
<212> TYPE: PRT
<213> ORGANISM: Homo sapiens

<400> SEQUENCE: 1

Cys Ala Leu Phe Phe Val
1               5

<210> SEQ ID NO 2
<211> LENGTH: 14
<212> TYPE: PRT
<213> ORGANISM: Homo sapiens

<400> SEQUENCE: 2

Asp Asp Gln Ser Val Ser Arg Lys Leu Ala Ala Ala Leu Glu
1               5                   10

<210> SEQ ID NO 3
<211> LENGTH: 7
<212> TYPE: PRT
<213> ORGANISM: Homo sapiens

<400> SEQUENCE: 3

Gly Ile Arg Val Met Glu Lys
1               5
```

```
<210> SEQ ID NO 4
<211> LENGTH: 7
<212> TYPE: PRT
<213> ORGANISM: Homo sapiens

<400> SEQUENCE: 4

Arg Lys Val Val Val Gly Ser
1               5

<210> SEQ ID NO 5
<211> LENGTH: 12
<212> TYPE: PRT
<213> ORGANISM: Homo sapiens

<400> SEQUENCE: 5

Cys Gly Tyr Arg Glu Val Ser Ser Ala Ala Leu Glu
1               5                   10

<210> SEQ ID NO 6
<211> LENGTH: 23
<212> TYPE: PRT
<213> ORGANISM: Homo sapiens

<400> SEQUENCE: 6

Asp Leu Ala His Asp Ala Leu Leu Ala Trp Gly Pro Pro Ser Ile Asn
1               5                   10                  15

Cys Leu Thr Leu Gly Ala Pro
            20

<210> SEQ ID NO 7
<211> LENGTH: 19
<212> TYPE: PRT
<213> ORGANISM: Homo sapiens

<400> SEQUENCE: 7

Arg Gly Leu Arg Cys Arg Ile Ser Pro Arg Ser His Pro Arg Asn Gln
1               5                   10                  15

Gln Thr Pro

<210> SEQ ID NO 8
<211> LENGTH: 19
<212> TYPE: PRT
<213> ORGANISM: Homo sapiens

<400> SEQUENCE: 8

Arg Gly Leu Gln Thr Gly Leu Glu Gly Ser Ala Trp Leu Leu Glu Cys
1               5                   10                  15

Gly Arg Ala

<210> SEQ ID NO 9
<211> LENGTH: 7
<212> TYPE: PRT
<213> ORGANISM: Homo sapiens

<400> SEQUENCE: 9

Arg Gln Asp Gly Arg His Gly
1               5

<210> SEQ ID NO 10
<211> LENGTH: 6
<212> TYPE: PRT
<213> ORGANISM: Homo sapiens

<400> SEQUENCE: 10
```

```
Val Ser Lys Arg Asp Leu
1               5

<210> SEQ ID NO 11
<211> LENGTH: 6
<212> TYPE: PRT
<213> ORGANISM: Homo sapiens

<400> SEQUENCE: 11

Ser Ser Tyr Ala Leu Ile
1               5

<210> SEQ ID NO 12
<211> LENGTH: 7
<212> TYPE: PRT
<213> ORGANISM: Homo sapiens

<400> SEQUENCE: 12

Ser Ile Gly His Arg Arg Glu
1               5

<210> SEQ ID NO 13
<211> LENGTH: 7
<212> TYPE: PRT
<213> ORGANISM: Homo sapiens

<400> SEQUENCE: 13

Gly Pro Gly Leu Lys Glu Met
1               5

<210> SEQ ID NO 14
<211> LENGTH: 6
<212> TYPE: PRT
<213> ORGANISM: Homo sapiens

<400> SEQUENCE: 14

Thr Ser Gln Leu Trp Cys
1               5

<210> SEQ ID NO 15
<211> LENGTH: 7
<212> TYPE: PRT
<213> ORGANISM: Homo sapiens

<400> SEQUENCE: 15

Arg Arg Ser Gly Lys Leu Leu
1               5

<210> SEQ ID NO 16
<211> LENGTH: 7
<212> TYPE: PRT
<213> ORGANISM: Homo sapiens

<400> SEQUENCE: 16

Gly Arg Glu Leu Arg Gly Gln
1               5

<210> SEQ ID NO 17
<211> LENGTH: 14
<212> TYPE: PRT
<213> ORGANISM: Homo sapiens

<400> SEQUENCE: 17

Gly Arg Arg Gly Gly Ala Lys Pro Ala Val Ala Ser Arg Arg
1               5                   10
```

```
<210> SEQ ID NO 18
<211> LENGTH: 7
<212> TYPE: PRT
<213> ORGANISM: Homo sapiens

<400> SEQUENCE: 18

Gly Asp Arg Arg Asp Ser Arg
1               5

<210> SEQ ID NO 19
<211> LENGTH: 7
<212> TYPE: PRT
<213> ORGANISM: Homo sapiens

<400> SEQUENCE: 19

Leu Asp Ser Ser Leu Phe Asn
1               5

<210> SEQ ID NO 20
<211> LENGTH: 7
<212> TYPE: PRT
<213> ORGANISM: Homo sapiens

<400> SEQUENCE: 20

Leu Ser Thr Asn Arg Phe Val
1               5

<210> SEQ ID NO 21
<211> LENGTH: 7
<212> TYPE: PRT
<213> ORGANISM: Homo sapiens

<400> SEQUENCE: 21

Val Gly Pro Ser Val Gly Pro
1               5

<210> SEQ ID NO 22
<211> LENGTH: 7
<212> TYPE: PRT
<213> ORGANISM: Homo sapiens

<400> SEQUENCE: 22

Lys Ser Met Ala Arg His Arg
1               5

<210> SEQ ID NO 23
<211> LENGTH: 6
<212> TYPE: PRT
<213> ORGANISM: Homo sapiens

<400> SEQUENCE: 23

Glu Gly Gly Asn Glu Val
1               5

<210> SEQ ID NO 24
<211> LENGTH: 7
<212> TYPE: PRT
<213> ORGANISM: Homo sapiens

<400> SEQUENCE: 24

Asp Gly Arg Ser Ser Arg Gly
1               5

<210> SEQ ID NO 25
```

```
<211> LENGTH: 6
<212> TYPE: PRT
<213> ORGANISM: Homo sapiens

<400> SEQUENCE: 25

Asp Arg Asn Arg Ser Ala
1               5

<210> SEQ ID NO 26
<211> LENGTH: 15
<212> TYPE: PRT
<213> ORGANISM: Homo sapiens

<400> SEQUENCE: 26

Phe Ser Gly Arg Arg Leu Val Ser Pro Arg Pro His Pro Ser Asn
1               5                   10                  15

<210> SEQ ID NO 27
<211> LENGTH: 13
<212> TYPE: PRT
<213> ORGANISM: Homo sapiens

<400> SEQUENCE: 27

Gly Gly Leu Arg Gly Gly Lys Leu Ala Ala Ala Leu Glu
1               5                   10

<210> SEQ ID NO 28
<211> LENGTH: 7
<212> TYPE: PRT
<213> ORGANISM: Homo sapiens

<400> SEQUENCE: 28

Gly Gly Asn Ala Asn Arg Arg
1               5

<210> SEQ ID NO 29
<211> LENGTH: 7
<212> TYPE: PRT
<213> ORGANISM: Homo sapiens

<400> SEQUENCE: 29

Gly Met Lys Gly Val Gln Leu
1               5

<210> SEQ ID NO 30
<211> LENGTH: 6
<212> TYPE: PRT
<213> ORGANISM: Homo sapiens

<400> SEQUENCE: 30

Gly Arg Gly Asp Arg Arg
1               5

<210> SEQ ID NO 31
<211> LENGTH: 6
<212> TYPE: PRT
<213> ORGANISM: Homo sapiens

<400> SEQUENCE: 31

Lys Val Ser Asp Ser Leu
1               5

<210> SEQ ID NO 32
<211> LENGTH: 7
<212> TYPE: PRT
<213> ORGANISM: Homo sapiens
```

<400> SEQUENCE: 32

Leu Ser Thr Arg Val Glu Arg
1               5

<210> SEQ ID NO 33
<211> LENGTH: 7
<212> TYPE: PRT
<213> ORGANISM: Homo sapiens

<400> SEQUENCE: 33

Gln Asn Asp Ser Ala Ser Gly
1               5

<210> SEQ ID NO 34
<211> LENGTH: 7
<212> TYPE: PRT
<213> ORGANISM: Homo sapiens

<400> SEQUENCE: 34

Arg Ala Ala Asn Thr Ala Arg
1               5

<210> SEQ ID NO 35
<211> LENGTH: 7
<212> TYPE: PRT
<213> ORGANISM: Homo sapiens

<400> SEQUENCE: 35

Ser Val Ala Pro Leu Arg Arg
1               5

<210> SEQ ID NO 36
<211> LENGTH: 7
<212> TYPE: PRT
<213> ORGANISM: Homo sapiens

<400> SEQUENCE: 36

Thr Ser Leu Lys Asp Asp Arg
1               5

<210> SEQ ID NO 37
<211> LENGTH: 15
<212> TYPE: PRT
<213> ORGANISM: Homo sapiens

<400> SEQUENCE: 37

Val Phe Ser Gly Val Glu Val Ser Ser Arg Pro His Ser Ser Asn
1               5                   10                  15

<210> SEQ ID NO 38
<211> LENGTH: 15
<212> TYPE: PRT
<213> ORGANISM: Homo sapiens

<400> SEQUENCE: 38

Val Gly Val Arg Ile Gly Gly Ser Leu Arg Pro His Ser Ser Asn
1               5                   10                  15

<210> SEQ ID NO 39
<211> LENGTH: 6
<212> TYPE: PRT
<213> ORGANISM: Homo sapiens

<400> SEQUENCE: 39

```
Val Ser Gly Ser Val Arg
1               5

<210> SEQ ID NO 40
<211> LENGTH: 5
<212> TYPE: PRT
<213> ORGANISM: Homo sapiens

<400> SEQUENCE: 40

Val Val Arg Ala Lys
1               5

<210> SEQ ID NO 41
<211> LENGTH: 7
<212> TYPE: PRT
<213> ORGANISM: Homo sapiens

<400> SEQUENCE: 41

Arg Ala Pro Gly Gly Glu Thr
1               5

<210> SEQ ID NO 42
<211> LENGTH: 7
<212> TYPE: PRT
<213> ORGANISM: Homo sapiens

<400> SEQUENCE: 42

Gln Ala Arg Asn Gly Gly Arg
1               5
```

BONE MARROW TARGETING PEPTIDES

RELATED APPLICATION

This application claims priority from U.S. Provisional Application No. 61/369,236, filed Jul. 30, 2010, the subject matter, which is incorporated herein by reference in its entirety.

TECHNICAL FIELD

This application relates to targeting moieties than can be used to target bone marrow, and more particularly, to peptides that can selectively target bone marrow and be used in targeting cells for bone marrow transplantation.

BACKGROUND

Promises of cures of a wide variety of diseases or tissue injuries by specific replacement of damaged or malfunctional tissues by use of totipotent, pluripotent or multipotent stem cells is on the horizon in clinical practice (see, e.g., Fuchs, et al., 2000, Cell, 100:143-156; Weissman et al., 2000, Cell, 100:157-168; Blau, et al., 2001, Cell, 105:829-841). To transmute a somatic cell into the variety of cell types needed for tissue regeneration and reconstruction in vertebrates is a realistic goal. In fact, tissues that were formerly considered incapable of extensive regeneration, such as brain, spinal cord, and cardiac muscle, now appear to be capable of reconstruction functionally, at least to some extent, by stem cell populations. Stem cells derived from the embryo and from adult tissues have been shown to have extensive potentials for self-renewal and differentiation. However, methods of targeting of stem cells to specific target tissues and their potential value for use in tissue reconstruction procedures require further study. Investigation in these areas may lead to realistic approaches in the future for stem cell therapy in a variety of human diseases, tissue injuries, and other clinical problems. In addition, efforts in tissue engineering and restorative surgery would be improved by advances in cell targeting technology. One of the cornerstones/obstacles in implementing this technology is being able to direct the cells or tissue, engineered in vitro, to the precise in vivo site were repair is needed.

SUMMARY

This application relates to a peptide for targeting bone marrow. The peptide can consist of about 5 to about 25 amino acids and include an amino acid sequence having a sequence identity selected from the group consisting of CALFFV (SEQ ID NO:1), DDQSVSRKLAAALE (SEQ ID NO:2), GIRVMEK (SEQ ID NO:3), RKVVVGS (SEQ ID NO:4), CGYREVSSAALE (SEQ ID NO:5), DLAHDALLAWGPPSINCLTLGAP (SEQ ID NO:6), RGLRCRISPRSHPRNQQTP (SEQ ID NO:7), RGLQTGLEGSAWLLECGRA (SEQ ID NO:8), RQDGRHG (SEQ ID NO:9), VSKRDL (SEQ ID NO:10), SSYALI (SEQ ID NO:11), SIGHRRE (SEQ ID NO:12), GPGLKEM (SEQ ID NO:13), TS-QLWC (SEQ ID NO:14) RRSGKLL, (SEQ ID NO:15) GRELRGQ (SEQ ID NO:16), GRRGGAKPAVASRR (SEQ ID NO:17), GDRRDSR (SEQ ID NO:18), LDSSLFN (SEQ ID NO:19), LSTNRFV (SEQ ID NO:20), VGPSVGP (SEQ ID NO:21), KSMARHR (SEQ ID NO:22), and EGGNEV (SEQ ID NO:23), and RAPGGET (SEQ ID NO:41).

In some aspects, the peptide can include an amino acid sequence having a sequence identity selected from the group consisting of CALFFV (SEQ ID NO:1), DDQSVSRKLAAALE (SEQ ID NO:2), GIRVMEK (SEQ ID NO:3), RKVVVGS (SEQ ID NO:4), CGYREVSSAALE (SEQ ID NO:5), SSYALI (SEQ ID NO:11), and SIGHRRE (SEQ ID NO:12).

In yet other aspects, the peptide can include an amino acid sequence having a sequence identity selected from the group consisting of CALFFV (SEQ ID NO:1), RKVVVGS (SEQ ID NO:4), RQDGRHG (SEQ ID NO:9), and RAPGGET (SEQ ID NO:41).

In other aspects, the peptide can include an amino acid sequence having a sequence identity of RKVVVGS (SEQ ID NO: 4).

In still other aspects, the peptide can be linked to a cell. The peptide can target the cell to bone marrow and enhance engraftment of the cell in and/or to the bone marrow. In some aspects, the cell can include a progenitor cell selected from the group consisting of a totipotent stem cell, pluripotent stem cell, multipotent stem cell, mesenchymal stem cell, hematopoietic stem cell, embryonic stem cell, embryonic germ cell, and endothelial progenitor cell. In other aspects, the cell can be an umbilical cord blood cell. The umbilical cord blood cell can be a CD34+ progenitor cell, a CD133+ progenitor cell, an endothelial progenitor cell, a hematopoietic stem cell, and/or a hemangioblast.

The application also relates to a composition for bone marrow transplantation. The composition includes an umbilical cord blood cells and a peptide linked to the umbilical cord blood cell. The peptide can target the umbilical cord blood cell to bone marrow and enhance engraftment of the umbilical cord blood cell when the composition is administered to a subject. The peptide consists of about 5 to about 25 amino acids and includes an amino acid sequence having a sequence identity selected from the group consisting of CALFFV (SEQ ID NO:1), DDQSVSRKLAAALE (SEQ ID NO:2), GIRVMEK (SEQ ID NO:3), RKVVVGS (SEQ ID NO:4), CGYREVSSAALE (SEQ ID NO:5), DLAHDALLAWGPPSINCLTLGAP (SEQ ID NO:6), RGLRCRISPRSHPRNQQTP (SEQ ID NO:7), RGLQTGLEGSAWLLECGRA (SEQ ID NO:8), RQDGRHG (SEQ ID NO:9), VSKRDL (SEQ ID NO:10), SSYALI (SEQ ID NO:11), SIGHRRE (SEQ ID NO:12), GPGLKEM (SEQ ID NO:13), TS-QLWC (SEQ ID NO:14) RRSGKLL, (SEQ ID NO:15) GRELRGQ (SEQ ID NO:16), GRRGGAKPAVASRR (SEQ ID NO:17), GDRRDSR (SEQ ID NO:18), LDSSLFN (SEQ ID NO:19), LSTNRFV (SEQ ID NO:20), VGPSVGP (SEQ ID NO:21), KSMARHR (SEQ ID NO:22), and EGGNEV (SEQ ID NO:23), and RAPGGET (SEQ ID NO:41).

In some aspects, the peptide can include an amino acid sequence having a sequence identity selected from the group consisting of CALFFV (SEQ ID NO: 1), DDQSVSRKLAAALE (SEQ ID NO:2), GIRVMEK (SEQ ID NO:3), RKVVVGS (SEQ ID NO:4), CGYREVSSAALE (SEQ ID NO:5), SSYALI (SEQ ID NO:11), and SIGHRRE (SEQ ID NO:12).

In yet other aspects, the peptide can include an amino acid sequence having a sequence identity selected from the group consisting of CALFFV (SEQ ID NO:1), RKVVVGS (SEQ ID NO:4), RQDGRHG (SEQ ID NO:9), and RAPGGET (SEQ ID NO:41).

In other aspects, the peptide can include an amino acid sequence having a sequence identity of RKVVVGS (SEQ ID NO: 4).

The umbilical cord blood cell can be a CD34+ progenitor cell, a CD133+ progenitor cell, an endothelial progenitor cell, a hematopoietic stem cell, and/or a hemangioblast.

DETAILED DESCRIPTION

Figure 1:
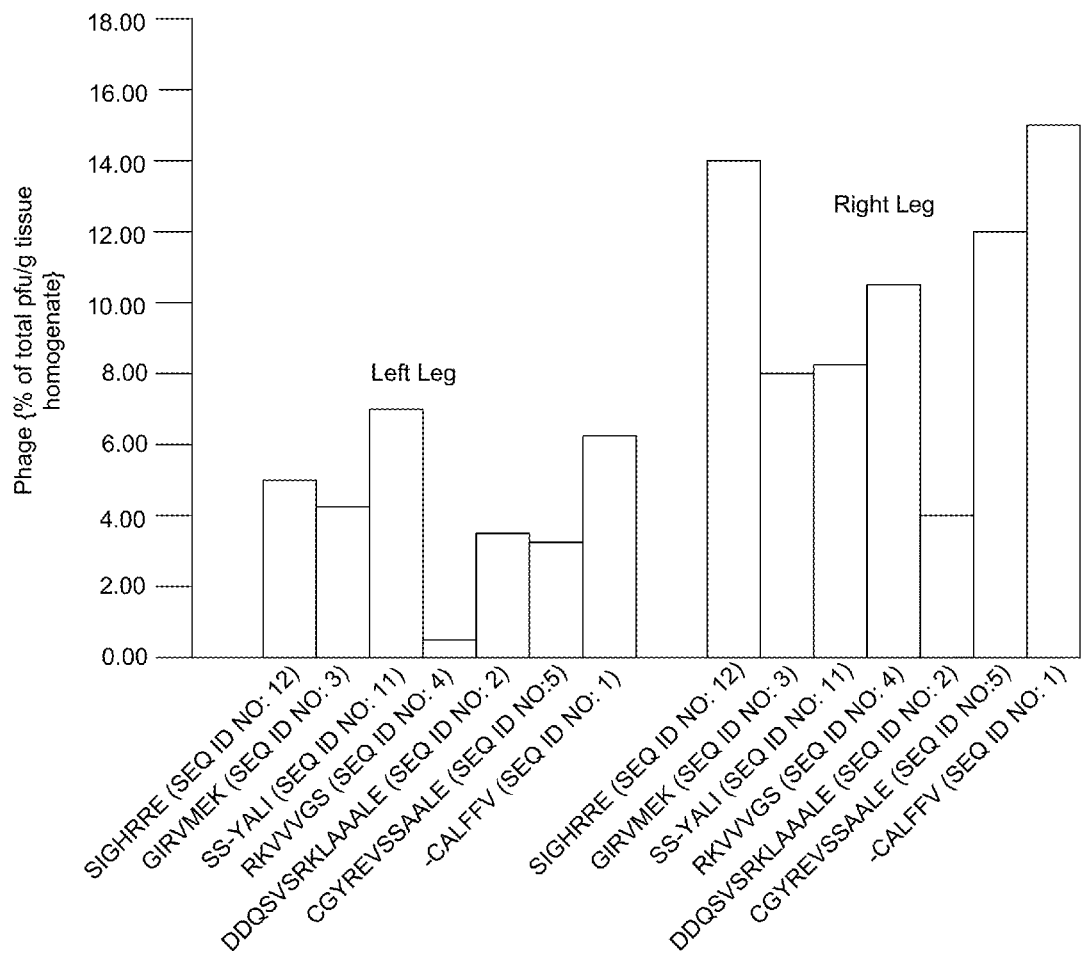
FIG. 1 illustrates the distribution of individual phage injected into mice whose right leg was irradiated. The amount of phage was normalized to tissue mass.

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "chondrogenic cells" includes chondrocytes and cells that differentiate into chondrocytes. The term may also refer to cells that are genetically altered or otherwise manipulated so as to become cells that produce substantial components of the cartilage matrix. The term "complex carbohydrates" herein include proteoglycans such as chondroitin sulfate, dermatan sulfate, heparin, heparan sulfate, hyaluronate, and keratan sulfate. The complex carbohydrates also include those polysaccharides which can be bound by lectins.

As used herein, the term "epitope" refers to a physical structure on a molecule that interacts with a selective component. In exemplary embodiments, epitope refers to a desired region on a target molecule that specifically interacts with a selectivity component.

As used herein, the term "homing peptide" or "targeting peptide" refers to a particular peptide that binds relatively specifically to an epitope of a target tissue or organ, following administration to a subject. In general, a homing peptide that selectively homes to a target tissue is characterized, in part, by detecting at least a 2-fold greater specific binding of the peptide to the target tissue as compared to a control tissue.

The term "immunogen" traditionally refers to compounds that are used to elicit an immune response in an animal, and is used as such herein. However, many techniques used to produce a desired selectivity component, such as the phage display and aptamer methods described below, do not rely wholly, or even in part, on animal immunizations. Nevertheless, these methods use compounds containing an "epitope," as defined above, to select for and clonally expand a population of selectivity components specific to the "epitope." These in vitro methods mimic the selection and clonal expansion of immune cells in vivo, and, therefore, the compounds containing the "epitope" that is used to clonally expand a desired population of phage, aptamers and the like in vitro are embraced within the definition of "immunogens."

As used herein, the term "lipophilic moiety" includes any lipid soluble long-chain fatty acid. For example, the lipophilic moiety includes a palmitoyl moiety, a myristoyl moiety, a margaroyl moiety, a stearoyl moiety, an arachidoyl moiety, an acetyl moiety, a butylyl moiety, a hexanoyl moiety, an octanoyl moiety, a decanoyl moiety, a lauroyl moiety, a palmitoleoyl moiety, a behenoyl moiety, and a lignoceroyl moiety.

The term "progenitor cell" as used herein, includes any totipotent stem cell, pluripotent stem cell, and multipotent stem cell, as well as any of their lineage descendant cells. The terms "stem cell" and "progenitor cell" are used interchangeably herein. The progenitor cell can derive from either embryonic tissues or adult tissues. Exemplary progenitor cells can be selected from, but not restricted to, totipotent stem cell, pluripotent stem cell, multipotent stem cell, mesenchymal stem cell, hematopoietic stem cell, pancreatic stem cell, cardiac stem cell, embryonic stem cell, embryonic germ cell, neural crest stem cell, kidney stem cell, hepatic stem cell, lung stem cell, hemangioblast cell, and endothelial progenitor cell. Additional exemplary progenitor cells are selected from, but not restricted to, de-differentiated chondrogenic cell, myogenic cell, osteogenic cell, tendogenic cell, ligamentogenic cell, adipogenic cell, and dermatogenic cell.

This application relates to peptides that can be used to target bone marrow in a subject. Targeting peptides that specifically bind organs or tissues have multiple applications including drug delivery, tissue labeling for diagnostics and, when combined with cell targeting technology, can be used to deliver repair cells to particular sites within the body. We identified a set of peptides that were selected for their affinity to bone marrow, with and without irradiation. These peptides not only show high affinity for bone marrow, but also show high affinity for the spleen, indicating that these peptides may generally target the hematopoietic system and possibly lymphoid organs as well. These peptides can be used in bone marrow transplantation therapies and methods to target transplanted cells to a subject's bone marrow. Advantageously, the targeted cells have enhanced or improved binding and engraftment compared cells that are not targeted.

In an embodiment of the application, the bone marrow targeting peptide can consist of about 5 to about 25 amino acids and include an amino acid sequence having a sequence identity selected from the group consisting of CALFFV (SEQ ID NO:1), DDQSVSRKLAAALE (SEQ ID NO:2), GIRVMEK (SEQ ID NO:3), RKVVVGS (SEQ ID NO:4), CGYREVSSAALE (SEQ ID NO:5), DLAHDALLAWG-PPSINCLTLGAP (SEQ ID NO:6), RGLRCRISPRSHPRN-QQTP (SEQ ID NO:7), RGLQTGLEGSAWLLECGRA (SEQ ID NO:8), RQDGRHG (SEQ ID NO:9), VSKRDL (SEQ ID NO:10), SSYALI (SEQ ID NO:11), SIGHRRE (SEQ ID NO:12), GPGLKEM (SEQ ID NO:13), TS-QLWC (SEQ ID NO:14), RRSGKLL, (SEQ ID NO:15) GRELRGQ (SEQ ID NO:16), GRRGGAKPAVASRR (SEQ ID NO:17), GDRRDSR (SEQ ID NO:18), LDSSLFN (SEQ ID NO:19), LSTNRFV (SEQ ID NO:20), VGPSVGP (SEQ ID NO:21), KSMARHR (SEQ ID NO:22), and EGGNEV (SEQ ID NO:23), and RAPGGET (SEQ ID NO:41).

In some aspects, the peptide can include an amino acid sequence having a sequence identity selected from the group consisting of CALFFV (SEQ ID NO:1), DDQSVSRK-LAAALE (SEQ ID NO:2), GIRVMEK (SEQ ID NO:3), RKVVVGS (SEQ ID NO:4), CGYREVSSAALE (SEQ ID NO:5), SSYALI (SEQ ID NO:11), and SIGHRRE (SEQ ID NO:12).

In yet other aspects, the peptide can include an amino acid sequence having a sequence identity selected from the group consisting of CALFFV (SEQ ID NO:1), RKVVVGS (SEQ ID NO:4), RQDGRHG (SEQ ID NO:9), and RAPGGET (SEQ ID NO:41).

In other aspects, the peptide can include an amino acid sequence having a sequence identity of RKVVVGS (SEQ ID NO: 4).

In other embodiments, the targeting peptides described herein may be modified to make them more resistant to cleavage by proteases. For example, the stability of targeting peptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting peptide may be of the D configuration. The switch from L to D amino acids neutralizes the digestion capabilities of many of the ubiquitous peptidases found in the digestive tract. Alternatively, enhanced stability of a targeting peptide comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting peptide may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting moiety without affecting the activity or specificity of the interaction with a desired target molecule.

The targeting peptides can be identified using various methods well known in the art. An exemplary method is the in vivo phage display method. Specifically, random peptide sequences are expressed as fusion peptides with the surface proteins of phage, and this library of random peptides are infused into the systemic circulation. After infusion into host mice, target tissues or organs are harvested, the phage is then isolated and expanded, and the injection procedure repeated at least two more times. Each round of injection includes, by default, a negative selection component, as the injected virus has the opportunity to either randomly bind to tissues, or to specifically bind to non-target tissues. Virus sequences that specifically bind to non-target tissues will be quickly eliminated by the selection process, while the number of non-specific binding phage diminishes with each round of selection.

Phage display technology provides a means for expressing a diverse population of random or selectively randomized peptides. Various methods of phage display and methods for producing diverse populations of peptides are well mown in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, *Meth. Enzymol.*, 217:228-257, Scott et al., *Science*, 249:386-390, and two peT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264,563). These or other well-known methods can be used to produce a phage display library, which can be subjected to the in vivo phage display method in order to identify a peptide that homes to bone marrow.

In vitro screening of phage libraries has previously been used to identify peptides that bind to antibodies or to cell surface receptors (see, e.g., Smith et al., 1993, *Meth. Enzymol.*, 217:228-257). For example, in vitro screening of phage peptide display libraries has been used to identify novel peptides that specifically bind to integrin adhesion receptors (see, e.g., Koivunen et al., 1994, *J. Cell Biol.* 124:373-380), and to the human urokinase receptor (Goodson et al., 1994, *Proc. Natl. Acad. Sci., USA* 91:7129-7133). However, such in vitro studies provide no insight as to whether a peptide that can specifically bind to a selected receptor in vitro also will bind the receptor in vivo or whether the binding peptide or the receptor are unique to a specific organ in the body.

In certain embodiments, the targeting peptides described herein can comprise a portion of a fusion protein. Such fusion protein may contain a tag that facilitates its isolation, immobilization, identification, or detection and/or which increases its solubility. In a preferred embodiment, the fusion protein comprises a targeting peptide, which selectively directs a cell, therapeutic agent, or diagnostic agent to a bone marrow. An exemplary fusion protein comprises a targeting peptide fused to the amino terminus of the Fc region of the human IgG sequence and to the carboxyl terminus of the oncostatin-M signal peptide.

The fusion protein may contain other tags, for example, glutathione Stransferase (GST), calmodulin-binding peptide, thioredoxin, maltose binding protein, HA, myc, poly arginine, poly His, poly His-Asp or FLAG tags. Additional exemplary tags include polypeptides that alter protein localization in vivo, such as signal peptides, type III secretion system-targeting peptides, transcytosis domains, nuclear localization signals, etc. In various embodiments, a targeting peptide described herein may comprise one or more tags, including multiple copies of the same tag or two or more different tags. It is also within the scope of the invention to include a spacer (such as a polypeptide sequence or a chemical moiety) between a targeting peptide and the tag in order to facilitate construction or to optimize its structural constraints. In another embodiment, the tagged peptide may be constructed so as to contain protease cleavage sites between the tag and the peptide in order to remove the tag. Examples of suitable endoproteases for removal of a tag, include, for example, Factor Xa and TEV proteases.

In certain embodiments, the targeting peptide can be used to deliver a therapeutic agent, diagnostic agent, and/or therapeutic cell to bone marrow and once delivered facilitate retention of, enhance engraftment of, and/or localization of the therapeutic agent, diagnostic and/or therapeutic cell to, at, and/or in the bone marrow.

In some embodiments described herein, a plurality of the targeting peptides can be coated on a cell to generate a cell delivery composition that includes the cell and the targeting peptides, where the targeting peptides is designed to bind to the bone marrow, or cells of the bone marrow and enhance engraftment of the cells in the bone marrow. In one example, the cell coating technique can be used to adherence of umbilical cord blood cells, such as CD34+ progenitor cells, to bone marrow by coating the cells with bone marrow specific peptides. This enhanced adherence of cells can increase the number of umbilical cord blood cells in the bone marrow, and, while not wishing to be bound to theory, it is expected that, the increased presence of cells at the bone marrow can improve the rate of recovery of the subject following bone marrow transplantation.

In certain embodiments, the cell coating technique can employ a linker to connect the cell to the targeting peptide. For example, protein A and protein G are useful linkers. In certain embodiments, the linker is connected to the cell by a lipophilic moiety, as in the case of palmitated protein A or protein G. The lipophilic moiety of the palmitate hydrocarbon chains makes it possible to coat the cell membrane with this linker by insertion into the outer leaflet of the phospholipid bilayer.

In some embodiments, the cell coated with the targeting peptides is a progenitor cell. As described herein, any progenitor cell that is suitable for the treating the bone marrow may be employed, including any totipotent stem cell, pluripotent stem cell, and multipotent stem cell, as well as any of their lineage descendant cells. The progenitor cell may derive from either embryonic tissues or adult tissues. In certain embodiments, the progenitor cell is selected from totipotent stem cell, pluripotent stem cell, multipotent stem cell, mesenchymal stem cell, hematopoietic stem cell, embryonic stem cell, embryonic germ cell, hemangioblast cell, and endothelial progenitor cell.

In other embodiments, the cell can be an umbilical cord blood cell, such as an umbilical cord blood progenitor cell. The umbilical cord blood cell can be, for example, a CD34+ progenitor cell, a CD133+ progenitor cell, an endothelial progenitor cell, a hematopoietic stem cell, and/or a hemangioblast.

Exemplary progenitor cells and methods for obtaining such cells are well known in the art and described in the following U.S. patents (prefaced by "US") and international patent applications (prefaced by "WO"): U.S. Pat. No. 5,130, 141; U.S. Pat. No. 5,453,357; U.S. Pat. No. 5,486,359; U.S. Pat. No. 5,589,376; U.S. Pat. No. 5,723,331; U.S. Pat. No. 5,736,396; U.S. Pat. No. 5,843,780; U.S. Pat. No. 5,877,299; U.S. Pat. No. 5,827,735; U.S. Pat. No. 5,906,934; U.S. Pat. No. 5,980,887; U.S. Pat. No. 6,200,806; U.S. Pat. No. 6,214, 369; U.S. Pat. No. 6,429,012; WO 00/53795; WO 00/02654; WO 00/78929; WO 01/11011; WO 01/42425; WO 02/86082.

In certain embodiments, the progenitor cell is an umbilical cord blood progenitor cell. Umbilical cord blood (UCB) cells have great potential as an alternative source of cells for bone marrow transplantation (BMT). UCB transplants result in fewer cases of graft vs. host disease (GVHD), are readily available from frozen stocks, and recipients tolerate a greater degree of human leukocyte antigen (HLA) mis-match.

In certain embodiments, the progenitor cell can express a cell surface marker or an extracellular matrix molecule. For example, the endothelial progenitor cell expresses a cell surface marker, i.e., fetal liver kinase-1 (Flk1). Another exemplary cell surface marker is p75 (a low affinity nerve growth factor receptor) for the neural crest stem cell. The cell surface marker or extracellular matrix molecule can be selected from, but not limited to, CD4, CD8, CD10, CD30, CD33, CD34, CD38, CD45, CD133, CD146, fetal liver kinase-1 (Flk1), C-Kit, Lin, Mac-1, Sca-1, Stro-1, Thy-1, Collagen types II or IV, O1, O4, N-CAM, p75, and SSEA.

In certain embodiments, the progenitor cells are immunologically matched to the subject who will receive them (e.g., similar HLA typing), and optionally, the cells are autologous, meaning that they are derived from the subject.

In certain embodiments, progenitor cells may be harvested and stored (e.g., by cryogen freezing), allowing banking of cells for later use.

In certain embodiments, a targeting peptide described herein may be directly associated with a progenitor cell. This may be achieved, for example, by modifying the targeting peptide with a lipophilic moiety to allow insertion into or association with the cell membrane. Direct attachment to a cell may also be achieved by covalently attaching the targeting peptide to another element that has an affinity for a marker on the surface of the cell to be coated, such as an extracellular protein or oligosaccharide. In other embodiments, a targeting peptide described herein may be indirectly associated with a progenitor cell. Indirect attachment may be achieved, for example, by providing a linker that associates with the progenitor cell to be coated and with the targeting peptides. Exemplary linkers include Protein G. Protein G is a highly stable surface receptor from Streptococcus sp. (Lancefield Group G), that has four 30 Fc-fragment binding sites for immunoglobulins and each molecule can bind 2 molecules ofIgG (Bjorck L and G. 1984; Boyle and Reis 1987). Another exemplary linker is Protein A, which also binds Fc fragments, but with a different range of specificities. Linkers may be modified to associate with a progenitor cell through any of the various approaches described above with respect to direct attachment of a targeting peptide. For example, the linker may be modified with a lipophilic moiety. In certain exemplary embodiment, the linker is palmitated protein G or palmitated protein A.

There are a wide range of lipophilic moieties with which linkers or targeting peptides may be derivatived, including without limitation, palmitoyl moiety, myristoyl moiety, margaroyl moiety, stearoyl moiety, arachidoyl moiety, acetyl moiety, butylyl moiety, hexanoyl moiety, octanoyl moiety, decanoyl moiety, lauroyl moiety, palmitoleoyl moiety, behenoyl moiety, and lignoceroyl moiety. Preferred lipophilic moieties include palmitoyl moiety, myristoyl moiety, and margaroyl moiety. A lipophilic group can be, for example, a relatively long chain alkyl or cycloalkyl (preferably n-alkyl) group having approximately 7 to 30 carbons. The alkyl group may terminate with a hydroxy or primary amine "tail". To further illustrate, lipophilic molecules include alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfullerenes, vitamins, polyethylene glycol or oligoethylene glycol, (C1C18)-alkyl phosphate diesters, —O—CH2-CH(OH)— O—(C12-CI8)-alkyl, conjugates with pyrene derivatives, esters and alcohols, other lipid molecules, cage structures such as adamantane and buckminsterfullerenes, and aromatic hydrocarbons such as benzene, perylene, phenanthrene, anthracene, naphthalene, pyrene, chrysene, and naphthacene.

Optionally, the lipophilic moiety can be a lipophilic dye suitable for use in the invention include, but are not limited to, diphenylhexatriene, Nile Red, N-phenyl-1-naphthylamine, Prodan, Laurodan, Pyrene, Perylene, rhodamine, rhodamine B, tetramethylrhodamine, Texas Red, sulforhodamine, 1,1'-didodecyl-3,3,3',3'tetramethylindocarbocyanine perchlorate, octadecyl rhodamine B and the BODIPY dyes available from Molecular Probes Inc. Other exemplary lipophilic moieties include aliphatic carbonyl radical groups such as decanoyl, dodecanoyl, dodecenoyl, tetradecadienoyl, decynoylor dodecynoyl.

The N-terminal amine of a protein can be modified preferentially relative to other amines in a protein because its lower pKa results in higher amounts of the reactive unprotonated form at neutral or acidic pH. Aryl halides, aldehydes and ketones, acid anhydrides, isocyanates, isothiocyanates, imidoesters, acid halides, N-hydroxysuccinimidyl (e.g., sulfo-NHS-acetate), nitrophenyl esters, acylimidazoles, and other activated esters and thioesters are among those known to react with amine functions.

There are a variety of chemical methods for the modification of many amino acid side chains, such as cysteine, lysine, histidine, aspartic acid, glutamic acid, serine, threonine, tyrosine, arginine, methionine, and tryptophan. Therefore a lipophilic moiety maybe attached to an amino acid other than at the N-terminus.

To illustrate, there are a large number of chemical cross-linking agents that are known to those skilled in the art. Heterobifunctional cross-linkers provide the ability to design more specific coupling methods for conjugating to proteins, thereby reducing the occurrences of unwanted side reactions such as homo-protein polymers. A wide variety of heterobifunctional cross-linkers are mown in the art. These include: succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-toluene (SMPT), N-succinimidyl 3-(2-pyridyldithio)propionate (SPDP), succinimidyl 6-[3-(2-pyridyldithio)propionate]hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exists a number of other cross-linking agents including homobifunctional and photoreactive cross-linkers. Disuccinimidyl suberate (DSS), bismaleimidohexane (BMH) and dimethylpimelimidate.2HCl (DMP) are examples of useful homobifunctional cross-linking agents, and bis-[β-(4-azidosalicylamido)ethyl]disulfide (BASED) and N-succinimidyl-6(4'-azido-2'-nitrophenyl-amino) hexanoate (SANPAH) are examples of useful photoreactive cross-linkers for use in this invention. For a recent review of protein coupling techniques, see Means et al. (1990), *Bioconjugate Chemistry*, 1:2-12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and release of NHS or sulfo-NHS as a by-product.

In certain embodiments, the lipophilic moiety employed is a lipid moiety. Generally, a "lipid" is a member of a heterogeneous class of hydrophobic substances characterized by a variable solubility in organic solvents and insolubility, for the most part, in water. The principal class of lipids that are encompassed within this invention are fatty acids and sterols (e.g., cholesterol). Derivatized proteins of the invention contain fatty acids which are cyclic, acyclic (i.e., straight chain), saturated or unsaturated, mono-carboxylic acids. Exemplary saturated fatty acids have the generic formula: $CH_3(CH_2)_nCOOH$. The following Table II lists examples of some fatty acids that can be derivatived conveniently using conventional chemical methods.

TABLE I

Exemplary Saturated and Unsaturated Fatty Acids

| Value of n | Common Name |
|---|---|
| Saturated Acids: $CH_3(CH_2)_n COOH$ | |
| 2 | Butyric acid |
| 4 | Caproic acid |
| 6 | Caprylic acid |
| 8 | Capric acid |
| 10 | Lauric acid |
| 12 | Myristic acid |
| 14 | palmitic acid |
| 16 | stearic acid |
| 18 | arachidic acid |
| 20 | behenic acid |
| 22 | lignoceric acid |
| Unsaturated Acids | |
| $CH_3CH=CHCOOH$ | crotonic acid |
| $CH_3(CH_2)_3CH=CH(CH_2)_7COOH$ | myristoleic acid |
| $CH_3(CH_2)_5CH=CH(CH_2)_7COOH$ | palmitoleic acid |
| $CH_3(CH_2)_7CH=CH(CH_2)_7COOH$ | oleic acid |
| $CH_3(CH_2)_3(CH_2CH=CH)_2(CH_2)_7COOH$ | linoleic acid |
| $CH_3(CH_2CH=CH)_3(CH_2)_7COOH$ | linolenic acid |
| $CH_3(CH_2)_3(CH_2CH=CH)_4(CH_2)_3COOH$ | arachidonic acid |

Other lipids that can be attached include branched-chain fatty acids and those of the phospholipid group such as the phosphatidylinositols (i.e., phosphatidylinositol 4-monophosphate and phosphatidylinositol 4,5-biphosphate), phosphatidycholine, phosphatidylethanolamine, phosphatidylserine, and isoprenoids such as farnesyl or geranyl groups.

In certain embodiments, the targeting peptide coated on the cell, can be directly or indirectly linked to a bioactive factor, such as a growth factor, a cytokine or a chemokine. Such bioactive factors may regulate the growth, differentiation, and/or function of the progenitor cell. The bioactive factors may be added with the progenitor cell. Optionally, the bioactive factors may be added subsequent to the delivery of the progenitor cell.

To illustrate, the bioactive factor may be selected from a growth factor of the transforming growth factor β superfamily (e.g., a TGFβ or a TGFα,); a bone morphogenetic protein (BMP, e.g., BMP2 or BMP4); cartilage-derived morphogenic proteins (CDMPs, e.g., CDMP-1 or CDMP-2) and growth differentiation factors (e.g., GDF5); angiogenic factors (e.g., angiogenin); platelet-derived cell growth factor (pD-ECGF); platelet-derived growth factors (pDGFs, e.g., PDGF-A, PDGFB, and PDGF-BB); vascular endothelial growth factor (VEGF); a member of the epidermal growth factor family (e.g., EGF, TGFs, and PDGFs); fibroblast growth 5 factors (e.g., bFGF); hepatocyte growth factors (HGFs); insulin-like growth factors (e.g., IGF-I and IGF-II); nerve growth factors (NGFs); colony-stimulating factor (e.g., CSF or GM-CSF); neurotrophin (e.g., NT-3, 4 or 5); growth hormones (GHs); interleukins (e.g., IL-1, IL-15); connective tissue growth factors (CTGFs); parathyroid hormone related proteins (PTHrp); chemokine; Wnt protein; Noggin; Gremlin; and mixtures of two or more of these factors.

In certain embodiments, a composition that includes a cell coated with targeting peptides can be prepared by coating the cell, such as a progenitor cell, with a linker and then contacting the linker such that the targeting peptide binds to the linker and is capable of targeting or binding to bone marrow when administered to a subject. The targeting peptide having been either directly or indirectly complexed and/or linked to the cell can be administered to a subject by a variety of means. Such administration methods, in view of this specification, are apparent to those of skill in the art. In certain embodiments, a composition that includes a cell coated with the targeting peptide is delivered to the subject by injection into blood. In other embodiments, a composition that includes the cell coated with the targeting peptide is delivered to the subject by injection into the target tissue, i.e., bone marrow. In still other embodiments, a composition that includes the cell coated with the targeting peptide is delivered to the subject by surgical implantation. In still other embodiments, a composition that includes the cell coated with the targeting peptide is delivered to the subject by subcutaneous injection. In yet other embodiments, a composition that includes the cell coated with the targeting peptide is delivered to the subject by intra-peritoneal injection. In yet other embodiments, a composition that includes the cell coated with the targeting peptide is delivered to the subject by intra-synovial injection.

In certain embodiments, a composition that includes the cell coated with the targeting peptide may be inserted into a delivery device which facilitates introduction by injection or implantation into the subjects. Such delivery devices may include tubes or intraluminal devices, e.g., catheters, for injecting cells and fluids into the body of a recipient subject. In a preferred embodiment, the tubes additionally have a needle, e.g., a syringe, through which a composition that includes the cell coated with the targeting peptide can be introduced into the subject at a desired location.

A composition that includes the cell coated with the targeting peptide may be prepared for delivery in a variety of different forms. For example, the composition may be suspended in a solution or gel or embedded in a support matrix when contained in such a delivery device. The composition may be mixed with a pharmaceutically acceptable carrier or diluent in which the cells described herein remain viable. Pharmaceutically acceptable carriers and diluents include saline, aqueous buffer solutions, solvents and/or dispersion media. The use of such carriers and diluents is well known in the art. The solution is preferably sterile and fluid. The solution can be stable under the conditions of manufacture and storage and preserved against the contaminating action of microorganisms such as bacteria and fungi through the use of, for example, parabens, chlorobutanol, phenol, ascorbic acid, thimerosal, and the like. Solutions may be prepared by incorporating cells as described herein in a pharmaceutically acceptable carrier or diluent and, as required, other ingredients enumerated above, followed by filtered sterilization.

In certain aspects, the targeting peptides can be used in bone marrow transplantation therapies. For example, the bone marrow transplantation may result from irradiation of bone marrow cells during treatment of cancer in a subject. The targeting peptide can be linked to bone marrow cells, progenitor cells, and/or umbilical cord blood cells and administered to a subject to treat or repopulated the irradiated bone marrow.

Another aspect of the application relates to compositions and methods of tissue engineering. Tissue engineering provides the opportunity to generate living substitutes for tissues and organs, which may overcome the drawbacks of classical tissue reconstruction.

In certain embodiments, a tissue engineering composition can include a progenitor cell, a targeting peptide that binds to bone marrow, and a biocompatible scaffold. Such tissue engineering composition generates a scaffold graft to be delivered to a bone injury. Optionally, tissue engineering composition may generate a scaffold graft that can each include one type of progenitor cell or multiple types of progenitor cells.

In other embodiments, the present invention provides a method of delivering a scaffold graft in a bone, comprising: a) linking a progenitor cell to a targeting peptides that binds to bone marrow; b) seeding the progenitor cell from (a) onto a scaffold, thereby forming a scaffold graft; and c) implanting the scaffold graft from (b) in direct contact with, or adjacent to bone marrow for a sufficient time, wherein cells of the bone marrow associate with the implanted scaffold graft, thereby to form new tissue. For example, the scaffold graft can be delivered in bone marrow by surgical implantation. Optionally, such methods may further comprise removing the scaffold graft from the subject. For example, the scaffold graft removed from the subject (i.e., the scaffold and the tissue it bears at the end of the implantation period) can then be re-grafted into another site.

As described herein, the biocompatible scaffold can consist of bioresorbable or non-bioresorbable materials. If the scaffold consists of a single bioresorbably material, it is preferably one that does not significantly resorb during the period of time when the target tissue is being laid down on or within it. Such scaffolds will generate a scaffold graft that includes living cells and essentially retain their shape and mechanical integrity. In some instances, it may be preferable to use scaffolds containing bioresorbable materials that lose, for example, less than a 2% of their weight during the same period. If the scaffold is constructed with two or more bioresorbable materials, it may be preferable to select the bioresorbable material that provides the scaffold with its structural integrity according to these criteria.

A wide range of bioresorbable materials is well known in the art, with varying in vivo resorption times. Moreover, the resorption time of a single material itself can also vary significantly with the molecular weight. By blending or copolymerizing different bioresorbable materials and/or by modifying the molecular weights of the materials, it is possible to tailor the resorption time of the bioresorbable material to the requirement at hand.

In certain embodiments, the bioresorbable materials for the biocompatible scaffold include bioresorbable polymers or copolymers that comprise the following monomers or mixtures of polymers and/or copolymers formed thereby: hydroxyl acids, particularly lactic acid; glycolic acid; caprolactone; hydroxybutyrate; dioxanone; orthoesters; orthocarbonates; aminocarbonates.

Optionally, the bioresorbable materials can also include natural materials such as collagen, cellulose, fibrin, hyaluronic acid, fibronectin, chitosan, or mixtures of two or more of these materials. The bioresorbable materials may also comprise devitalized xenograft and/or devitalized allograft. Bioresorbable ceramics can also be included within the scaffold. Preferred bioresorbable materials include poly(lactic acid), poly(glycolic acid), polydioxanone, polyhydroxybutyrate, and poly(trimethylene carbonate), or mixtures thereof. Poly(lactic acid) has good mechanical strength and does not resorb quickly. Thus, its mechanical properties can be retained for a time sufficient for tissue in-growth to occur (at which point the tissue can assume some, if not all, of the load-bearing function of the scaffold (see A. G. A. Coombes and M.e. Meikle, "Resorbable Synthetic Polymers as Replacements for Bone Graft," *Clinical Materials*, 17:35-67, 1994). Samples of poly(lactic acid) have been shown to lose only one or two percent of their weight over a 12-week trial.

In certain embodiments, the non-bioresorbable materials for the biocompatible scaffold include polyesters, particularly aromatic polyesters, such as polyalkylene terephthalates; polyamides; polyalkenes such as polyethylene and polypropylene; poly(vinyl fluoride), polytetrafluoroethylene carbon fibres; silk (natural or synthetic); carbon fibre; glass; and mixtures of these materials. An advantage of non-bioresorbable materials is that they essentially retain their initial mechanical properties. Thus, their strength does not lessen over time.

Preferably, the biocompatible scaffold is at least partially porous so that it allows tissue in-growth. When the scaffold contains interconnected pores that are evenly distributed, cells can infiltrate essentially all areas of the scaffold during the period of implantation. The pore diameter is determined by, in part, the need for adequate surface area for tissue in-growth and adequate space for nutrients and growth factors to reach the cells. In certain embodiments, the biocompatible scaffold may comprise a woven, non-woven (fibrous material), knitted, braided material, a foam, a sponge, a dendritic material, or a mixture of two or more of these. Optionally, the scaffold can be planar in form, cut or otherwise formed, if necessary, to an appropriate shape. For example, the scaffold can form a quadrilateral, circle, triangle, or other geometric shape in plan view.

In certain embodiments, the biocompatible scaffold can include certain additional components. For example, the scaffold may include bioactive factors, such as growth factors, cytokines or chemokines.

In other embodiments, hydrogels can also be included in the biocompatible scaffold. For example, the hydrogel can be incorporated within and/or around the scaffold prior to implantation to facilitate the transfer of cells and other biological material (e.g., growth factors) from the surrounding tissue into the scaffold. Hydrogels include positively charged, negatively charged, and neutral hydrogels, and can be either saturated or unsaturated. Examples of hydrogels are TETRONICS™ and POLOXAMINES™, which are poly(oxyethylene)poly(oxypropylene) block copolymers of ethylene diamine; polysaccharides, chitosan, poly(vinyl amines), poly(vinyl pyridine), poly(vinyl imidazole), polyethylenimine, poly-L-lysine, growth factor binding or cell adhesion molecule binding derivatives, derivatized versions of the above (e.g., polyanions, polycations, peptides, polysaccharides, lipids, nucleic acids or blends, block-copolymers or combinations of the above or copolymers of the corresponding monomers); agarose, methylcellulose, hydroxyproylmethylcellulose, xyloglucan, acetan, carrageenan, xanthangum/locust beangum, gelatine, collagen (particularly Type 1), PLURONICS™, POLOXAMERS™, POLY(N-isopropylacrylmide), and N-isopropylacryhnide copolymers.

The following examples are for the purpose of illustration only and are not intended to limit the scope of the claims, which are appended hereto.

EXAMPLE 1

In order to identify bone marrow specific peptides, this laboratory conducted a screening for peptides using phage display. The primary goal of this screening was to develop targeting peptides that could be used on conjunction with cell targeting methodologies for the delivery of repair cells to bone marrow or other hematopoietic organs.

C57BU6 mice had their right leg irradiated then, 24 h later, a phage library was injected and allowed to circulate, bone marrow was then harvested and the phage pool isolated. Phage were amplified and injected into the next mouse, and this process repeated a total of five times. The phage pool was then analysed from irradiated and non-irradiated legs and the sequences determined. Individual phage were then amplified, injected into irradiated mice and tissue distribution assessed. Table 1 lists the different peptides that came out of the sequencing from plaques plated after the last injection. Most of the bone marrow peptides did not show up in the lung, and some of the bone marrow peptides showed up multiple times. Most of the lung sequences remained in the lung samples, except for 2 that showed up in bone marrow. From these results, several peptides were selected for more detailed analysis (highlighted in yellow) and were injected separately into mice whose right leg was irradiated. FIG. 1 shows the results for those mice for each of the 6 peptide sequences. Most of the peptides showed an increased signal in irradiated leg, with the exception of DDQSVSRKLAAALE (SEQ ID NO:2). The most striking difference between irradiated and non-irradiated legs was with the peptide RKVVVGS (SEQ ID NO:4) which showed approximately 15× the signal in the irradiated leg.

TABLE II

| Peptide Sequence | | L. Leg (Non-IRR) | R. Leg (IRR) | Lung |
|---|---|---|---|---|
| -CALFFV | (SEQ ID NO: 1) | | 4 | 1 |
| DDQSVSRKLAAALE | (SEQ ID NO: 2) | | 3 | |
| GIRVMEK | (SEQ ID NO: 3) | | 2 | |
| RKVVVGS | (SEQ ID NO: 4) | | 1 | |
| -CGYREVSSAALE | (SEQ ID NO: 5) | | 1 | |
| DLAHDALLAWGPP SINCLTLGAP | (SEQ ID NO: 6) | | 1 | |
| RGLRCRISPRSHP RNQQTP | (SEQ ID NO: 7) | | | |
| RGLQTGLEGSAWL LECGRA | (SEQ ID NO: 8) | | 1 | |
| RQDGRHG | (SEQ ID NO: 9) | | 1 | |
| V-SKRDL | (SEQ ID NO: 10) | | 1 | |
| SS-YALI | (SEQ ID NO: 11) | | 5 | |
| SIGHRRE | (SEQ ID NO: 12) | 1 | | |
| GPGLKEM | (SEQ ID NO: 13) | 4 | | |
| TS-QLWC | (SEQ ID NO: 14) | 4 | | |
| RRSGKLL | (SEQ ID NO: 15) | 2 | | |
| GRELRGQ | (SEQ ID NO: 16) | 1 | | |
| GRR-GGAKPAVASRR | (SEQ ID NO: 17) | 1 | | |
| GDRRDSR | (SEQ ID NO: 18) | 1 | | |
| LDSSLFN | (SEQ ID NO: 19) | 1 | | |
| LSTNRFV | (SEQ ID NO: 20) | 1 | | |
| VGPSVGP | (SEQ ID NO: 21) | 1 | | |
| KSMARHR | (SEQ ID NO: 22) | 1 | | 1 |
| EGGN-EV | (SEQ ID NO: 23) | 1 | | 1 |
| DGRSSRG | (SEQ ID NO: 24) | | | 1 |

TABLE II-continued

| Peptide Sequence | | L. Leg (Non-IRR) | R. Leg (IRR) | Lung |
|---|---|---|---|---|
| DRN-RSA | (SEQ ID NO: 25) | | | 1 |
| FSGRRLVSPRPHPSN | (SEQ ID NO: 26) | | | 1 |
| GGL-RGGKLAAALE | (SEQ ID NO: 27) | | | 1 |
| GGNANRR | (SEQ ID NO: 28) | | | 1 |
| GMKGVQL | (SEQ ID NO: 29) | | | 1 |
| GRGDR-R | (SEQ ID NO: 30) | | | 1 |
| KVSD-SL | (SEQ ID NO: 31) | | | 1 |
| LSTRVER | (SEQ ID NO: 32) | | | 1 |
| QNDSASG | (SEQ ID NO: 33) | | | 1 |
| RAANTAR | (SEQ ID NO: 34) | | | 1 |
| SVAPLRR | (SEQ ID NO: 35) | | | 1 |
| TSLKDDR | (SEQ ID NO: 36) | | | 1 |
| VFSGVEVSSRPHSSN | (SEQ ID NO: 37) | | | 1 |
| VGVRIGGSLRPHSSN | (SEQ ID NO: 38) | | | 1 |
| VSGSVR | (SEQ ID NO: 39) | | | 1 |
| VVRAK | (SEQ ID NO: 40) | | | 1 |

These results identify a series of peptides that preferentially bind bone marrow and several that increase their binding in irradiated bone marrow. One peptide, RKVVVGS (SEQ ID NO:4), showed a marked increase in binding in irradiated legs and minimal binding in non-irradiated legs. In addition, when isolated RKVVVGS (SEQ ID NO:4) phage is injected into whole body irradiated mice, it showed highly increased binding to spleen, which may indicate a general affinity for hematopoietic organs.

EXAMPLE 2

In this example, we show umbilical cord blood (UCB) cell engraftment efficiency can be improved through a novel cell targeting methodology. Using phage display screening, as shown in this example, we identified a set of peptide sequences that preferentially bind bone marrow. One of these sequences has been engineered into a cell coating peptide (CCP) that contains a targeting sequence, a biotinylated tracking segment, and a lipid moiety for integration into cell membranes. We show that this CCP increases UCB cell binding to mouse bone marrow by about 6 to about 7 times. Based on these results, bone marrow-targeting sequences with high affinities to bone marrow can be used to produce CCPs that can enhance UCB binding to bone marrow and thus increase engraftment efficiency.

This example includes two distinct aspects of targeting UCB cells: One is to increase the numerical binding of UCB cells in bone marrow using CCPs, which is quantified using qRT-PCR of human ALU sequences, and the second is to determine if this increase in cell numbers results in increased engraftment. If positive, these results will show that CCP-coated UCB cells engraft more efficiently than do non-treated or control (random) CCP-coated UCB cells. In addition, the UCB titering studies will indicate the degree to which engraftment is enhanced by CCP-coating. If CCP treatment improves the engraftment of UCB cells, this could have a major impact on the use of UCB cells for BMT in adult patients and provide a source of cells for BMT for patients who lack an appropriate HLA-matched donor.

Validate and Select Bone Marrow-Binding Peptides

Figure 2:
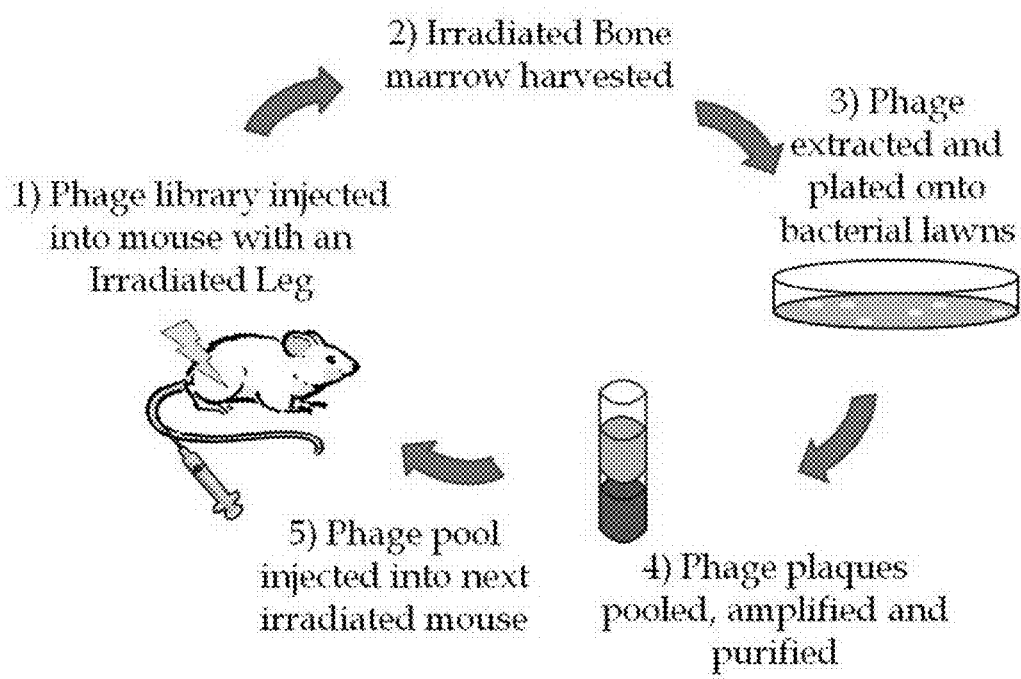
FIG. 2 illustrates schematic view of a phage screening strategy in accordance with an aspect of the application. The entire procedure was repeated 5 times to eliminate non-specific phage. On the fifth extraction, phage plaques were isolated from multiple organs and individually collected, expanded and sequenced.

The screening methodology employed for isolating bone marrow-binding peptide sequences via phage display is illustrated in FIG. 2. Included in our screening strategy was the idea of obtaining some bone marrow-binding peptides that had high affinity for irradiated bone marrow, which, although not a required feature for targeting UCB cells to marrow, could be useful for engraftment into hosts where radiation treatment is part of the conditioning regimen. After the 5th round of phage injections, phage was isolated from lungs and from irradiated and non-irradiated bone marrow and sequenced (20 plaques per organ isolate). Sequences were assessed to determine whether they showed up repeatedly, indicating high affinity to a specific tissue; or showed up in multiple organs, indicating lack of specificity. Only a few sequences were found in multiple organs and, more importantly, only bone marrow-derived plaques showed multiple hits for specific sequences, indicating specificity.

This initial screen is only the first step in selecting sequences for peptide synthesis. A summary of the complete selection process/criteria for determining which sequences will be used for synthesis into CCPs is as follows: 1. The initial sequencing screen; 2. A second, "Playoff screen" to confirm bone marrow specificity (described below); 3. Degree of amino acid sequence hydrophobicity (hydrophobic sequences are difficult to synthesize and purify); 4. Sequence length (longer sequences are more expensive); and, 5. Nucleotide sequence ambiguity. "Ambiguity" indicates sequences whose nucleotide sequence includes a stop codon, which can occur due to a frame shift, but is not easily interpretable. Several ambiguous sequences have already been encountered. However, even phage containing ambiguous sequences will not be completely discarded, since those phage surface peptides can be identified using Edmund degradation, if needed.

Table III highlights nine peptide sequences among the 60 phage plaques analyzed. Seven of these peptides were exclusively found to bind to either irradiated BM or control BM. For example, the sequences GIRVMEK (SEQ ID NO:3), DDQSVSRKLAAALE (SEQ ID NO:2), SIGHRRE (SEQ ID NO:12), CALFFV (SEQ ID NO:1) and SS-YALI (SEQ ID NO:11) are all of interest because of multiple hits in either irradiated or control bone marrow. The level of interest in CALFFV (SEQ ID NO: 1) was somewhat muted because the identical sequence showed up in lung. The sequence QARNGGR (SEQ ID NO:42) was eliminated because it showed no bone marrow specificity and was only detected in the lung—there were many others like this. Even though the sequence DDQSVSRKLAAALE (SEQ ID NO:2) is of interest because of the multiple hits in irradiated bone marrow, it was not selected for an initial round of synthesis because the sequence is relatively long, which significantly increases costs. The sequence SS-YALI (SEQ ID NO:11) is an example of an ambiguous sequence that contains an internal stop codon, indicated by the dash. As a result, the SS-YALI (SEQ ID NO:11) sequence was dropped from consideration for an initial round of synthesis. It should be noted that a BLAST search of the selected peptides did not immediately reveal any apparent reason for a particular affinity for a peptide to a specific tissue. In addition, more plaques can be selected from bone marrow extracts that have been stored at −80° C., and can be sequenced, if needed, to look for more bone marrow multi-hit sequences.

TABLE III

Phage sequence results

| AA Sequence | | Sequence copy number | | |
|---|---|---|---|---|
| | | Irr BM | C BM | Lung |
| GIRVMEK | (SEQ ID NO: 3) | 2 | 0 | 0 |
| DDQSVSRKLAAALE | (SEQ ID NO: 2) | 3 | 0 | 0 |
| SIGHRRE | (SEQ ID NO: 12) | 0 | 4 | 0 |
| CALFFV | (SEQ ID NO: 1) | 4 | 0 | 1 |
| RKVVVGS | (SEQ ID NO: 4) | 1 | 0 | 0 |
| RAPGGET | (SEQ ID NO: 41) | 1 | 0 | 0 |
| RQDGRHG | (SEQ ID NO: 9) | 1 | 0 | 0 |
| SS-YALI | (SEQ ID NO: 11) | 5 | 1 | 0 |
| QARNGGR | (SEQ ID NO: 42) | 0 | 0 | 1 |

Irr = irradiated; BM = bone marrow; C = control; AA = amino acid

Figure 3:
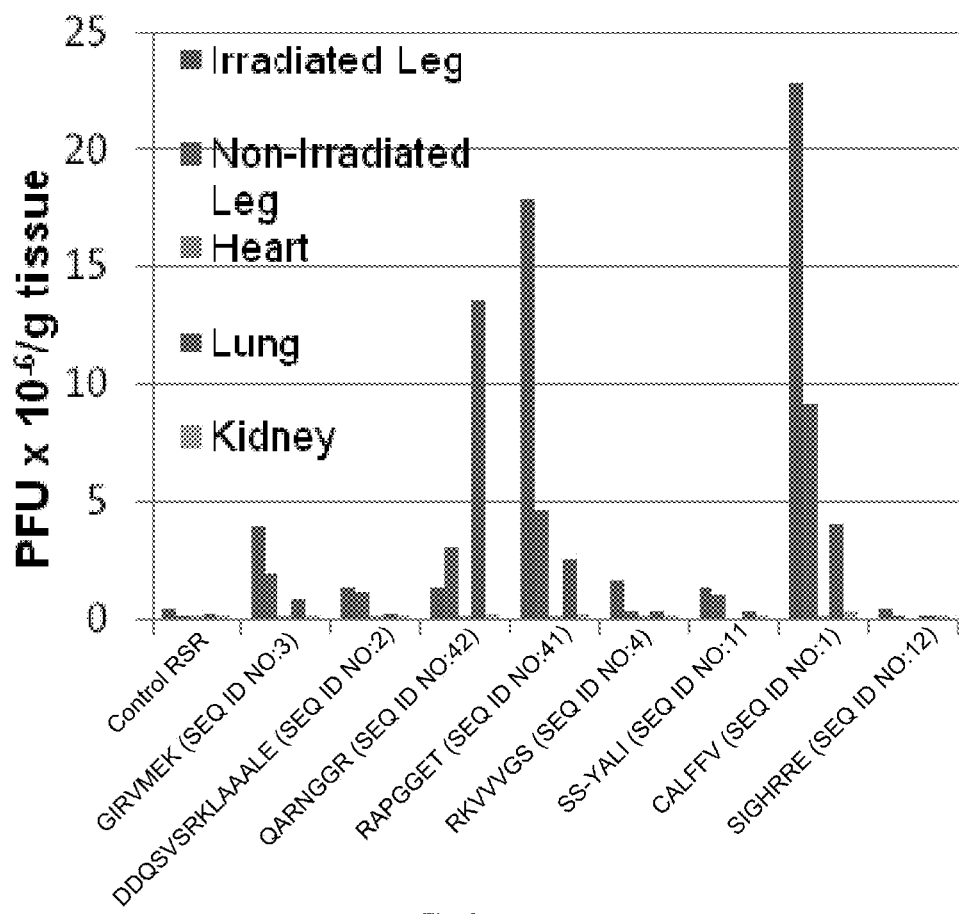
FIG. 3 illustrates a chart showing the results of a phage "playoff screen" where equimolar amounts of phage were injected into a mouse and plaque forming units (PFU) quantified. Control phage (RSR) showed low levels in all organs while a phage that was isolated from lung (QARNGGR (SEQ ID NO: 42)) showed high levels in lung and low levels in bone marrow.

We conducted a "playoff screen" to confirm bone marrow-targeting specificity. To perform a Playoff Screen, selected phage, along with a randomly selected phage from the pre-selected phage pool, were injected at equi-molar amounts into irradiated and non-irradiated mice, the bone marrows extracted, weighed and assayed for phage titer per gram of tissue; an example of the results of a Playoff Screen is shown in FIG. 3. While the data shown here are from only a single mouse, the results were important in several aspects. For one, the control "RSR" phage showed minimal bone marrow binding or binding to any of the other organs. However, one of the selected phage, SIGHRRE (SEQ ID NO: 12), also showed minimal phage titers in the marrow, so the SIGHRRE (SEQ ID NO: 12) sequence was also dropped from the list of sequences to be synthesized into a CCP. Importantly, none of the selected sequences showed significant phage titers in either heart or kidney tissues, indicating preferential binding to bone marrow. It is not surprising that many of the sequences showed some binding to lung, since lung is the first major organ that these peptides see after tail vein injection. The peptide QARNGGR (SEQ ID NO: 42) showed the highest level of lung binding and, more importantly, showed greater titers in the lung than in bone marrow, so this sequence has been eliminated from further study. These results outline how peptides are first identified using phage display, and then re-tested for specificity and, thereby, selected for peptide synthesis and incorporation into Cell Coating Peptide (CCP) molecules.

Synthesis and Quality Testing of CCP Molecules

Figure 4:
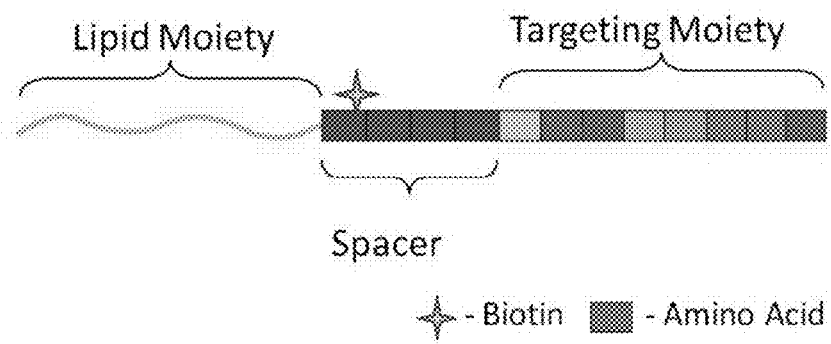
FIG. 4 illustrates a cell coating peptide (CCP) design showing the target-specific amino acids (targeting moiety) connected to a spacer moiety containing a biotin-labeled amino acid, and a lipid moiety for insertion into the cell membrane.

The CCP molecule has three primary components: One, the targeting peptide sequence; two, a linker sequence containing a biotinylated amino acid; and, three a lipid moiety for integration into the cell membrane (FIG. 4). Once synthesized, all CCP molecules are tested for purity and molecular weight using HPLC and mass spectroscopy (located in the Puget Sound Blood Center); for their ability to coat UCB CD34+ cells using flow cytometry, for any toxicity effects on progenitors using MTT and hematopoietic colony forming unit (CFU) assays.

Sequences from this initial round of selection (CALFFV (SEQ ID NO:1), RAPGGET (SEQ ID NO:41), RKVVVGS (SEQ ID NO: 4) and control RSR) were contracted out to commercial vendors for synthesis into CCPs. One single-hit sequence from bone marrow, RKVVVGS (SEQ ID NO:4), termed "RKV", was successfully synthesized, purified, and its molecular weight validated by mass spectroscopy. Flow cytometry using FITC-labeled Streptavidin was used to demonstrate that RKV was able to coat cells efficiently, and MTT assays showed no toxic effects on coated cells (data not shown).

For this study, we will synthesize an additional three CCP molecules that contain the peptide sequences, CALFFV (SEQ ID NO:1), RAPGGET (SEQ ID NO:41) and RQDGRHG (SEQ ID NO:9), along with the RSR control sequence. These new CCPs will be quality control tested (mass spectroscopy, cell coating capacity, and toxicity) prior to testing for their ability to target CD34+ UCB cells to bone marrow.

Quantification of Bone Marrow-Targeting of UCB Cells Coated with CCP Molecules

To test the efficiency of cellular targeting to the marrow, NOD/SCID mice will be sub-lethally irradiated with 250 cGy and injected with $1.0 \times 10^6$ UCB CD34+ cells coated with one of the 4 different bone marrow CCPs. This will include 3 newly-synthesized and the RKV CCP already available, CD34+ cells painted with a negative control peptide or with non-coated control CD34+ UCB cells. At 3 weeks post-injection, the mice will be sacrificed and blood, spleen, lungs, liver and bone marrow collected for analysis by qRT-PCT of human-specific ALU sequences. Five mice per group and at least 3 different UCB donors will be used to account for donor variability. CCPs that promote binding to bone marrow are predicted to show significantly higher ALU sequence signal in the bone marrow than in the control, but should have ALU signal values equivalent to negative control values in the liver and lungs. A positive binding result in the spleen is not unexpected, given our preliminary results and the fact that spleen is a site of HSC engraftment.

Figure 5:
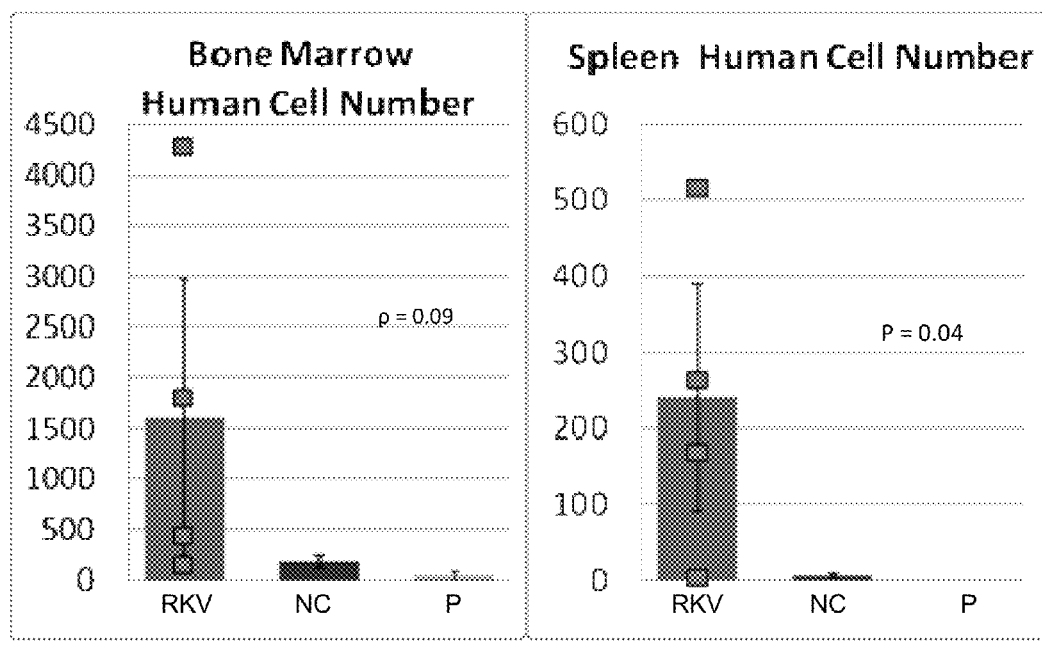
FIG. 5 illustrates a chart showing ALU qRT-PCR quantification of human UCB cell numbers. The y-axis indicates human cell numbers calculated from a human cell standard curve. RKV=RKV-coated human UCB cells; NC=Non-coated human UCB cells; P=Plasma-injected. ρ values are from Student's t test between RKV and NC samples. The squares indicate the individual values for the RKV samples.

Preliminary spleen and bone marrow-targeting of UCB cells has already been conducted with the RKV peptides as a CCP molecule (RKV-CCP). UCB cells were isolated using a discontinuous Percol gradient, red blood cells were lysed with ammonium chloride, and the cells were incubated at 37° C. for a total of 10 min with RKV-CCP molecule (30 µg/ml), centrifuged, washed and stored at 4° C. until injected. Progenitors from two separate UCB units were coated and tested. Mice were sub-lethally irradiated with 250 cGy and injected with $1.0 \times 10^8$ RKV-CCP coated or non-coated UCB cells, or plasma-only control; 2 mice per group per UCB sample for a total of 4 mice per injection group. Bone marrow, spleen and blood were collected 3 weeks post injection. qRT-PCR was then conducted to assess human ALU sequences. The number of human cells found in the marrow was derived from a qRT-PCR standard curve of known amounts of human cell mixed with murine UCB cells. The results showed that the bone marrows of mice injected with human UCB cells coated with RKV had ~7× more human-derived cells compared to control non-coated cells injected with the same dose (FIG. 5), and while not rising to the typical level of statistical significance, the results showed a strong statistical trend with a ρ value equal to 0.09. Plasma-injected mice had essentially no signal. Even though results showed enhanced UCB cell numbers in the spleen compared to uncoated UCB cells at a statistically significant level, the magnitude of UCB cell numbers was approximately 6 times higher in bone marrow compared to spleen.

Optimal Coating of Selected CCP

CCPs that have been tested and shown to increase bone marrow binding will be tested for optimal CCP coating density. The selected CCP(s) will be used to coat UCB cells at 100%, 75%, 50% and 25% of maximal coating, injected into sub-lethally irradiated mice, as described previously, and the bone marrow, spleen, lungs and kidneys harvested and analyzed by qRT-PCR of human ALU sequences. This will be used to determine the amount of cell coating that is optimal for targeting UCB cells to bone marrow. Our initial assumption is that greater coating will yield greater binding to bone marrow.

UCB Engraftment Efficiency and Limiting Dilution Analysis

The optimal coating concentration for the selected CCP will be used to coat CD34+ UCB cells and engraftment levels will be tested relative to random CCP-coated CD34+ UCB cells and untreated CD34+ UCB cells. Five mice per group will be injected with $1.0 \times 10^3$, $1.0 \times 10^4$, $5.0 \times 10^4$, $1.0 \times 10^5$ and $1.0 \times 10^6$ CD34+ UCB cells. At 8 weeks post-injection, mice will be sacrificed, and the blood, bone marrow and spleens will be collected. Peripheral blood, spleen and marrow will be assayed for human cell engraftment using human-specific antibodies to CD45 and CD34 and examined by flow cytometry. Murine marrow will be scored as positive only when the number of human CD45+ cells present after transplant is >0.1% of the total marrow and when CD34+ cells are present in the marrow. Mice that do not achieve both of these criteria will be scored as negative. The frequency of negative mice will be used to calculate the frequency of SCID-repopulating cells (SRCs) in the starting population. This will be done by using Poisson statistics and a weighted-mean method with iterative procedures to determine the best linear fit and standard errors of this function by using the software program, L-calc from StemCell Technologies. Multi-lineage engraftment will also be evaluated by co-staining marrow cells from recipient mice with antibody to human CD45 and one of the following antibodies: CD36, Glycophorin A, CD33, CD14, CD41, CD19 and CD3. To quantify the level of lymphohematopoietic reconstitution, the percent of cells expressing lymphocyte (i.e., CD19, CD3), myelocyte (i.e., CD33), erythrocyte (i.e., CD36, gylcophorin A), and megakaryocyte (i.e., CD41, CD61) associated antigens within the human CD45+ cell gate will be determined by flow cytometric analysis. Bone marrow will also be assessed for human cells using qRT-PCR for human ALU sequences.

Sustained Engraftment Efficiency

To measure the ability of coated UCB progenitors from primary NOD/SCID recipients to repopulate secondary recipients, ~8 weeks post-transplant bone marrow cells will be harvested from primary recipients of CCP-coated CD34+ cells that demonstrate the highest engraftment. Next, $4\text{-}6 \times 10^6$ cells will be infused into secondary recipients. At 2-3 months post-injection the secondary mice will be sacrificed and the blood, bone marrow and spleens will be analyzed as described above.

We expect to find that the UCB CD34+ cells coated with CCPs will enhance transplant efficiency. We also expect that UCB CD34+ cells coated with CCPs that have the highest binding efficiencies to bone marrow will also have the highest short-term and sustained engraftment levels.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A peptide for targeting bone marrow, the peptide consisting of an amino acid sequence of RKVVVGS (SEQ ID NO:4).

2. A composition for targeting bone marrow, the composition comprising a peptide consisting an amino acid sequence of RKVVVGS (SEQ ID NO:4).

3. The composition of claim 2, further comprising a cell, the peptide targeting the cell to bone marrow when the composition is administered to a subject.

4. The composition of claim 3, wherein the cell comprises a progenitor cell selected from the group consisting of a totipotent stem cell, pluripotent stem cell, multipotent stem cell, mesenchymal stem cell, hematopoietic stem cell, embryonic stem cell, embryonic germ cell, neural crest stem cell, and endothelial progenitor cell.

5. The composition of claim 3, wherein the cell comprises an umbilical cord blood cell.

6. A composition for bone marrow transplantation, the composition comprising:
an umbilical cord blood cell; and
a peptide linked to the umbilical cord blood cell, the peptide targeting the umbilical cord blood cell to bone marrow when the composition is administered to a subject, the peptide consisting of an amino acid sequence of RKVVVGS (SEQ ID NO:4).

7. The composition of claim 6, wherein the umbilical cord blood cell comprises at least one of a CD34+ progenitor cell, a CD133+ progenitor cell, an endothelial progenitor cell, a hematopoietic stem cell, and/or a hemangioblast.

* * * * *